US 6,951,951 B2
United States Patent
Beria et al.
(10) Patent No.: US 6,951,951 B2
(45) Date of Patent: Oct. 4, 2005

(54) PROCESS FOR PREPARING DISTAMYCIN DERIVATIVES

(75) Inventors: Italo Beria, Nerviano (IT); Paolo Cozzi, Milan (IT); Nicola Mongelli, Milan (IT); Fabrizio Orzi, Milan (IT)

(73) Assignee: Pharmacia Italia S.p.A., Milan (IT)

( * ) Notice: Subject to any disclaimer, the term of this patent is extended or adjusted under 35 U.S.C. 154(b) by 420 days.

(21) Appl. No.: 10/312,261

(22) PCT Filed: Jun. 14, 2001

(86) PCT No.: PCT/EP01/06762

§ 371 (c)(1),
(2), (4) Date: Dec. 24, 2002

(87) PCT Pub. No.: WO02/02523

PCT Pub. Date: Jan. 10, 2002

(65) Prior Publication Data

US 2004/0082759 A1 Apr. 29, 2004

(30) Foreign Application Priority Data

Jul. 4, 2000 (GB) .............................................. 0016447

(51) Int. Cl.$^7$ ............................................. C07D 295/00
(52) U.S. Cl. ........................................ 548/537; 548/530
(58) Field of Search ............................... 548/530, 537, 548/312.1, 312.4, 312.7, 313.7, 558

(56) References Cited

U.S. PATENT DOCUMENTS

| | | | | |
|---|---|---|---|---|
| 5,596,105 A | * | 1/1997 | Mongelli et al. | ............ 548/518 |
| 5,646,177 A | | 7/1997 | Koch et al. | |
| 5,880,097 A | | 3/1999 | Kauvar et al. | |
| 6,177,408 B1 | * | 1/2001 | Cozzi et al. | ................... 514/17 |

FOREIGN PATENT DOCUMENTS

| | | |
|---|---|---|
| EP | 0 246 868 A1 | 11/1987 |
| EP | 0 265 719 A1 | 5/1988 |
| EP | 0 388 948 A1 | 9/1990 |
| EP | 0 420 121 A1 | 4/1991 |
| GB | 2 178 036 A | 2/1987 |
| WO | WO 90 11277 A | 10/1990 |
| WO | WO 96 05196 A | 2/1996 |
| WO | WO 97 28123 | 8/1997 |
| WO | WO 97 43258 | 11/1997 |
| WO | WO 98 04524 A | 2/1998 |
| WO | WO 98 21202 A | 5/1998 |
| WO | WO 99 34796 A | 7/1999 |
| WO | WO 99/50266 | 10/1999 |
| WO | WO 00 06541 | 2/2000 |
| WO | WO 00/06542 | 2/2000 |
| WO | WO 01 40181 A | 6/2001 |
| WO | WO 01 85144 A2 | 11/2001 |

OTHER PUBLICATIONS

Sola F et al: "The antitumor efficacy of cytotoxic drugs is potentiated by growth-factor-complexing molecule" Cancer Chemotherapy and Pharmacology, vol. 43, No. 3, 1999, pp. 241–246, XP002104215. ISSN: 0344–5704.

Zou J P et al: "Distamcyin A derivatives potentiate tumor-necrosis factor activity via the modulation of tyrosine phosphorylation" International Journal Fo Cance, New York, NY, US, vol. 72, No. 5, 1997, pp. 810–814, XP002104217 ISSN: 0020–7136.

Tagliabue G et al: "Combination of the New Minor Groove Alkylator Tallimustine and Melphalan" European Journal of Cancer, Pergamon Press, Oxford, GB, vol. 33, No. 2, Feb. 1997, pp. 284–287, XP004282511 ISSN: 0959–8049.

Baraldi, Pier Giovanni et al: "Synthesis and antitumor activity of novel distamycin derivatives" Bioorg. Med. Chem. Lett. (1996), 6(11), 1241–1246 XP004134862 p. 1241, paragraph 2 example SCHEME1 p. 1244, paragraph 1 table 1 p. 1244, paragraph 4 –p. 1245, paragraph 1.

Cozzi P et al: XP004200573 "Cytotoxic alpha–Bromoacrylic Derivatives of Distamycin Analogues Modified at the Amidino Moiety" Bioorganic & Medicinal Chemistry Letters, Oxford, GB, vol. 10, No. 11, Jun. 2000, pp. 1273–1276, ISSN: 0960–894X.

Cozzi P et al: XP004200572 "Cytotoxic Halogenoacrylic Derivatives of Distamcyin A" Bioorganic & Medicinal Chemistry Letters, Oxford, GB, vol. 10, No. 11, Jun. 2000, pp. 1269–1272, ISSN: 0960–894X.

Catharina J A Van Moorsel et al: XP002110339 "Gemcitabine: Futrue Prospects of Single–Agent and Combination Studies" Oncologist, Alphamed Press, US, vol. 2, No. 3, 1997, pp. 127–134, ISSN: 1083–7159.

Budavari S (ed): XP002191966 "The Merck Index (12th Edition)" Merck Index, Encyclopedia of Chemicals, Drugs, and Biologicals, 13th. Edition 1996, Whitehouse Station, Merck & Co, US, vol. ED. 13, 2001, p. 4206 ISBN: 0–911910–12–3.

(Continued)

*Primary Examiner*—Bruce R. Campell
*Assistant Examiner*—Andrew D. Kosar
(74) *Attorney, Agent, or Firm*—Scully, Scott, Murphy & Presser

(57) ABSTRACT

A process for preparing distamycin derivatives possessing antitumor activity, by starting from distamycin A itself, is described. The process involves the preparation of the novel intermediates of formula (III)

(III)

11 Claims, No Drawings

OTHER PUBLICATIONS

Mosconi A M et al: XP004282426 "Combination Therapy with Gemcitabine in Non–small Cell Lung Cancer" European Journal of Cancer, Pergamin Press, Oxford, GB, vol. 33, Jan. 1997, pp. S14–S17, ISSN: 0959–8049.

D'Alessio, Roberto et al: "Structure–activity relationship of novel distamycin A derivatives: Synthesis and antitumor activity" Bioorg. Med. Chem. Lett. (1994), 4(12), 1467–72, XP000671766.

Stewart D J et al: "Non–Chemotherapeutic Agents that Potentiate Chemotherapy Efficacy" Cancer Treatment Reviews, vol. 16, No. 1, 1989, pp. 1–40, XP001039737 ISSN: 0305–7372 p. 18, paragraph 3 –p. 19, paragraph 1.

Colella, G. et al: "Mismatch repair deficiency is associated with resistance to DNA minor groove alkylating agents" BR. J. Cancer (1999), 80(3/4), 338–343, XP001039733.

Geroni C et al: "PNU–166196: A novel antitumor agent whose cytotoxicity is enhanced in tumor cells with high levels of glutathione." TUMORI, vol. 86, No. 4 Suppl. 1, Jul. 2000, pp. 41–42, XP001039871 XV Congress of the Italian Cancer Society; Turin, Italy; Oct. 05–07, 2000 ISSN: 0300–8916, Abstract only.

Tsuchida S et al: "Elevation of the Placental Glutathione–S–Transferase Form GST–PI in Tumor Tissues and the Levels in Sera of Patients with Cancer" Cancer Research, vol. 49, No. 18, 1989, pp. 5225–5229, XP001039783 ISSN: 0008–5472 abstract p. 5225, col. 1, paragraph 1 p. 5228, col. 1, paragraph 1 p. 5228, col. 2, paragraph 1.

Cozzi P: "A new class of cytotoxic DNA minor groove binders: alpha–halogenoacrylic derivatives of pyrrolecarbamoyl oligomers." FARMACO, (Jan.–Feb. 2001) 56 (1–2) 57–65., XP001039805 abstract p. 58, col. 2, paragraph 4 p. 59, col. 1, paragraph 1 figure 5 p. 60, col. 1, paragraph 2 –p. 61, col. 1, paragraph 4 tables 2,3 p. 62, col. 2, paragraph 3 figures 9, 10 table 5 p. 63, col. 1, paragraph 1 –col. 2, paragraph 2.

Baraldi, Pier Giovanni et al: "Synthesis and Antitumor Activity of New Benzoheterocyclic Derivatives of Distamycin A" J. Med. Chem. (2000), 43(14), 2675–2684 , Jul. 13, 2000, XP001039581 abstract p. 2676, col. 1; tables p. 2676, col. 1, paragraph 1 tables 1,2 p. 2678, col. 2, paragraph 5 –p. 2679, col. 1, paragraph 1 p. 2680, col. 2, paragraph 3.

Boger et al., "Total Synthesis of Distamycin A and 2640 Analogues: A Solution–Phase Combinatorial Approach to the Discovery of New Bioactive DNA Binding Agents and Development of a Rapid, High–Throughput Screen for Determining Relative DNA Binding Affinity or DNA Binding Sequence Selectivity", J. Am. Chem. Soc. 2000, 122, 6382–6394.

Cytotoxic α–Bromoacrylic Derivatives of Distamycin Analogues Modified at the Amidino Moiety P. Cozzi, et al. (2000) Bioorg. Med. Chem. Letters, 10(11) pp. 1273–1276.

* cited by examiner

PROCESS FOR PREPARING DISTAMYCIN DERIVATIVES

The present invention relates to a process for preparing distamycin derivatives and, more in particular, to a process for preparing a key intermediate in the preparation of a variety of distamycin derivatives bearing a terminal guanidino group.

Distamycin A, whose formula is reported below

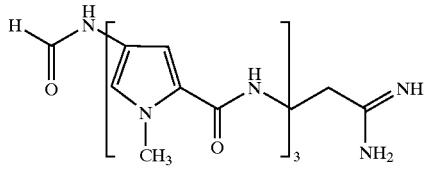

belongs to the family of the pyrroleamidine antibiotics and it is reported to interact reversibly and selectively with DNA-AT sequences, thus interfering with both replication and transcription. See, for a reference, Nature, 203, 1064 (1964); FEBS Letters, 7 (1970) 90; Prog. Nucleic Acids Res. Mol. Biol., 15, 285 (1975).

Several analogues to distamycin are known in the art as antitumor agents.

As an example, the international patent application WO 98/04524 in the name of the Applicant itself, discloses novel distamycin derivatives, having valuable biological properties as antitumor agents, wherein the distamycin formyl group is replaced by an acryloyl moiety and the amidino group is replaced by several nitrogen-containing ending groups among which is guanidino.

These latter compounds, hereinafter shortly referred to as distamycin-guanidines, are also disclosed in the following patent applications WO 97/28123, WO 97/43258, WO 99/50265, WO 99/50266, WO 99/64413 and WO 01/40181 (claiming priority from British patent application no. 9928703.9), all in the name of the applicant itself, and herewith incorporated by reference.

Representative of this class of compounds, optionally in the form of pharmaceutically acceptable salts are, for instance:

1. N-(5-{[(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide (internal code PNU 166196);
2. N-(5-{[(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)amino]carbonyl}-1-methyl-1H-pyrrol-3-yl)-4-[(2-chloroacryloyl)amino]-1-methyl-1H-pyrrole-2-carboxamide;
3. N-(5-{[(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)amino]carbonyl}-1-methyl-1H-pyrrol-3-yl)-4-[(2-bromoacryloyl)amino]-1-methyl-1H-imidazole-2-carboxamide;
4. N-(5-{[(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide;
5. N-(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)-4-({[4-({4-[bis(2-chloroethyl)amino]benzoyl}amino)-1-methyl-1H-pyrrol-2-yl]carbonyl}amino)-1-methyl-1H-pyrrole-2-carboxamide;
5. N-(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)amino]carbonyl}-1-methyl-1H-pyrrol-3-yl)-3-({4-[bis(2-chloroethyl)amino] benzoyl}amino)-1-methyl-1H-pyrazole-5-carboxamide;
7. N-(5-{[(5-{[(2-{[amino(imino)methyl]amino}ethyl) amino]carbonyl}-1-methyl-1H-pyrrol-3-yl)amino] carbonyl}-1-methyl-1H-pyrrol-3-yl)-4-[({4-[(-3-{4-[bis (2-chloroethyl)amino]phenyl}-2-propenoyl)amino]-1-methyl-1H-pyrrol-2-yl}carbonyl)amino]-1-methyl-1H-pyrrole-2-carboxamide.

All of these compounds, and analogues thereof, are prepared according to a known chemical process comprising, essentially, the condensation reaction between a properly activated carboxylic acid derivative with a polypyrroleamido framework bearing the desired guanidino group. This latter guanidino intermediate, in its turn, is prepared according to a rather troublesome step-by-step procedure which implies, substantially, several acylation reactions of 2-carboxy-4-amino-pyrroles which are obtained through reductions of the corresponding nitro derivatives, in a serial manner.

For a general reference to the above process for preparing distamycin-guanidines see, for instance, the aforementioned WO 98/04524.

In this respect, we have surprisingly found that the said distamycin-guanidines can be advantageously prepared through a process which, by starting from distamycin A itself, allows to obtain the desired products in high yields and purity and according to a limited number of steps.

Therefore, it is a first object of the present invention a process for preparing a poly-pyrroleamido derivative of formula (I)

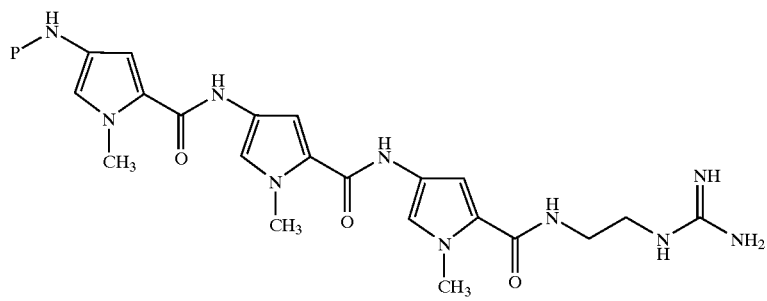

wherein P is a hydrogen atom or a suitable amino protecting group, which process comprises:
a) hydrolysing distamycin A under basic conditions and properly protecting the resulting amino group so as to obtain a compound of formula (II)

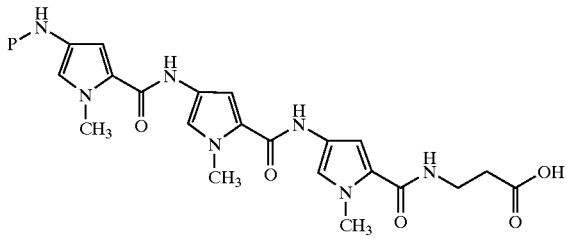

wherein P is a suitable amino protecting group;
b) reacting the compound of formula (II) with diphenylphosphorylazide (DPPA), so as to obtain a compound of formula (III)

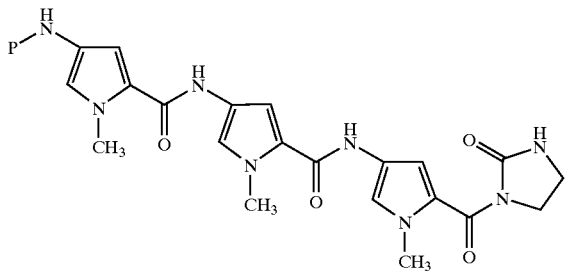

c) hydrolysing under basic conditions the compound of formula (III) so as to obtain the derivative of formula (IV)

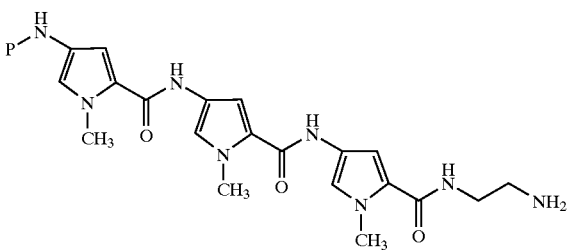

d) reacting the compound of formula (IV) with a suitable guanylating agent so as to obtain the derivative of formula (V)

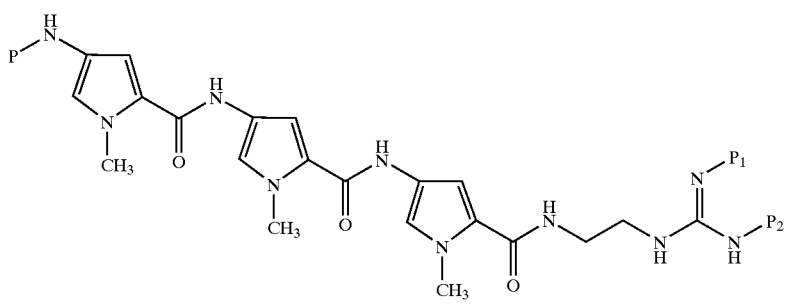

wherein $P_1$ and $P_2$, the same, are hydrogen atoms or amino protecting groups equal or different to P and, when $P_1$ and $P_2$ are other than hydrogen atoms,
e) deprotecting the guanidino and the amino group so as to obtain the derivative of formula (I).

The process object of the present invention allows to obtain the compounds of formula (I), as useful intermediates in the synthesis of a variety of distamycin-guanidines, under mild conditions and in high yields and purity.

In addition, it enables the preparation of the aforementioned compounds without the need of carrying out several steps and/or isolating intermediate amino derivatives which could lead to undesired by-products.

In the present description, unless otherwise specified, with the term amino protecting groups P, $P_1$ and $P_2$ we intend any protecting group conventionally used in organic synthesis to protect free amino functions which could undergo unwanted side reactions.

Typical examples of amino protecting groups are, for instance, formyl, benzyl and tert-butoxycarbonyl. Particularly preferred is tert-butoxycarbonyl.

From the foregoing, it is clear to the man skilled in the art that any of the above process steps comprising protection/deprotection of amino groups are carried out according to conventional techniques.

As an example, deprotection of tert-butoxycarbonylamino to amino can be carried out under acidic conditions, for instance in the presence of hydrochloric or trifluoroacetic acid in an organic solvent, e.g. dichloromethane, ethanol, methanol or mixtures thereof, at a temperature ranging from about 20° C. to about 40° C.

The hydrolysis of distamycin A, in step (a), is carried out under conventional basic conditions, for instance with sodium hydroxide, in an organic solvent such as a lower alcohol, preferably methanol.

The reaction temperature may vary from about 20° C. to about 100° C. and the reaction time from about 12 to about 72 hours. In step (a), the amino protected group of formula (II) is obtained according to conventional methods known in the art. As an example, when P is a formyl group, the reaction is carried out with formamide and ethyl formate. The reaction temperature may vary from about 20° C. to about 120° C. and for a period varying from about 1 to about 24 hours.

When P is tert-butoxycarbonyl, the reaction is carried out in an organic solvent such as dichloromethane (DCM), tetrahydrofuran or, preferably, dimethylformamide, with di-tert-butyldicarbonate in the presence of an organic base, e.g. diisopropylethylamine or triethylamine.

The reaction temperature may vary from about 20° C. to about 100° C. and the reaction time from about 1 to about 24 hours.

In step (b), the compound of formula (III) is obtained by reacting the compound of formula (II) with a slight excess, e.g. from 1 to 2 eq., of diphenylphosphorylazide (DPPA), in presence of an excess, e.g. from 1 to 2 eq., of an organic base such as diisopropylethylamine (DIPEA) or pyridine or, more preferably, triethylamine (TEA), in an organic solvent, e.g. THF, acetonitrile or dimethylformamide, this latter solvent being preferred.

The reaction temperature may vary from about 20° C. to about 100° C. and the reaction time from about 1 to about 24 hours.

In step (c), the hydrolysis reaction of compound (III) is carried out under basic conditions, preferably in the presence of a conventional hydroxide, e.g. sodium hydroxide, in a mixture of water/organic solvent such as, for instance, tetrahydrofuran (THF); acetonitrile or dimethylformamide (DMF). Water/DMF admixtures are preferred.

The reaction is carried out at temperatures varying from about 0° C. to about 70° C. and from about 1 to about 24 hours.

In step (d), suitable guanylating agents are those commercially available or easily prepared according to known methods such as, for instance, S-methylisothiourea, O-methylisourea, 3,5-dimethylpyrazole-1-carboxamidine or N-N'-di-tert-butoxycarbonyl-N"triflylguanidine of formula (VI) below.

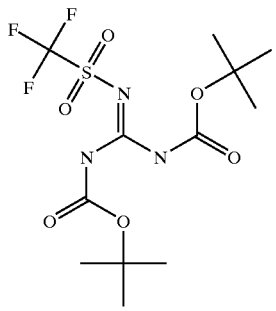

(VI)

According to the guanylating agent used in the process, the $P_1$ and $P_2$ groups in the compound of formula (V) can be selected among hydrogen atoms or amino protecting groups.

As an example, when using the above guanylating agent of formula (VI), both $P_1$ and $P_2$ represent tert-butoxycarbonyl groups.

The reaction of step (d) is carried out in an organic solvent, preferably methanol, in the presence of an excess of an organic base, for instance from 2 to 4 eq. of diisopropylethylamine (DIPEA) or, more preferably, triethylamine (TEA), in a range of temperature comprised from about –20° C. to about 100° C.

All the reagents of the process of the present invention are commercially available or easily preparable according to known methods.

As an example, the aforementioned compound N-N'-di-tert-butoxycarbonyl-N"triflylguanidine of formula (VI) can be prepared as reported in J. Org. Chem. 1998, 63-3804-5. Likewise, the starting material distamycin A, can be prepared according to a microbiological process as described, for instance, by Arcamone et al. in Nature 203, 1064 (1964).

According to a further aspect of the process, the intermediate compounds of formula (III)

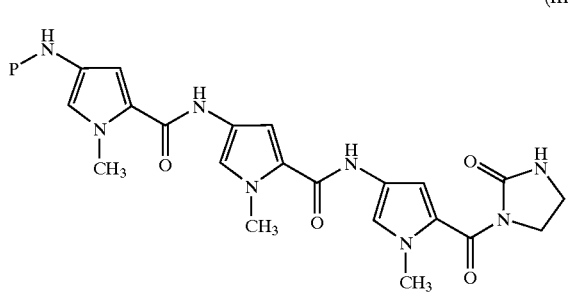

wherein P is hydrogen or a suitable amino protecting group, preferably formyl, benzyl or tert-butoxycarbonyl, are novel and, hence, represent a further object of the present invention.

As above reported, the compound of formula (I) is a useful intermediate in the preparation of distamycin-guanidines possessing antitumor activity.

It is therefore a further object of the invention a process for preparing distamycin-guanidines of formula (VII)

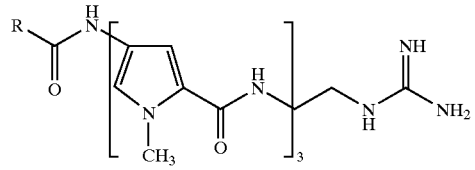

wherein
R is selected from the group consisting of:

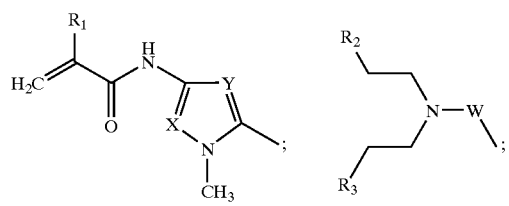

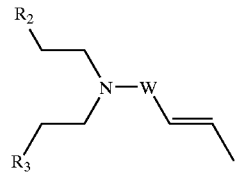

wherein
$R_1$ and $R_2$ are chlorine or bromine atoms;
$R_3$ is hydrogen, chlorine or bromine;
X and Y, the same or different, are selected from nitrogen atoms or CH groups;
W is phenylene or a benzocondensed 5 or 6 membered heterocycle with 1 or 2 heteroatoms selected among N, O or S, both of which being optionally further substituted by lower alkyl groups; or pharmaceutically acceptable salts thereof; which process comprises:
a) hydrolysing distamycin A under basic conditions and properly protecting the resulting amino group so as to obtain a compound of formula (II)

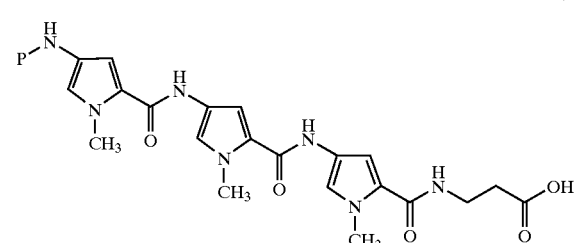

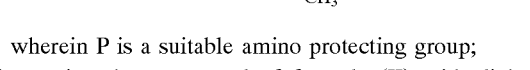

wherein P is a suitable amino protecting group;
b) reacting the compound of formula (II) with diphenylphosphorylazide (DPPA), so as to obtain a compound of formula (III)

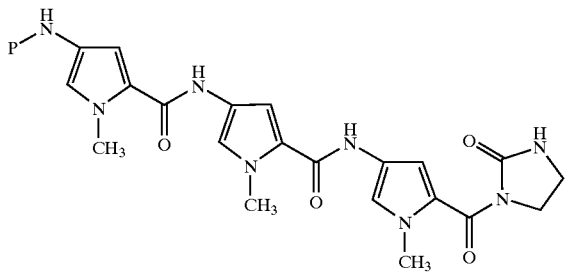

c) hydrolysing under basic conditions the compound of formula (III) so as to obtain the derivative of formula (IV)

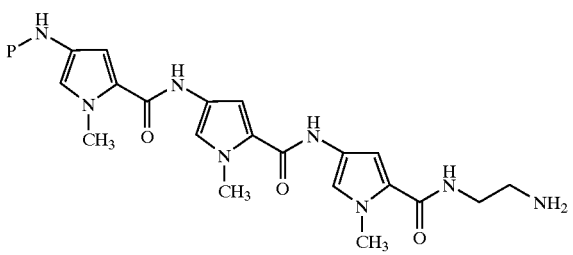

d) reacting the compound of formula (IV) with a suitable guanylating agent so as to obtain the derivative of formula (V)

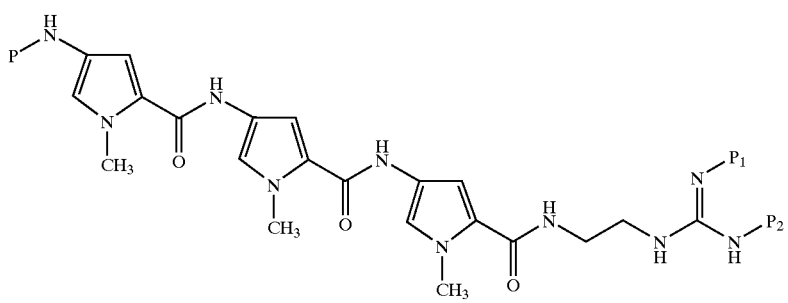

wherein $P_1$ and $P_2$, the same, are hydrogen atoms or amino protecting groups equal or different to P and, when $P_1$ and $P_2$ are other than hydrogen atoms, e) deprotecting the guanidino and the amino group so as to obtain the derivative of formula f) acylating the compound of formula (I) with a carboxylic derivative of formula

R-COZ  (VIII)

wherein R has the above reported meanings and Z is hydroxy or a suitable leaving group, so as to obtain the compounds of formula (VII) and, whenever desired, converting them into pharmaceutically acceptable salts.

The acylation reaction according to step (f) is carried out according to conventional techniques.

As an example, the reaction between a compound of formula (I) and a compound of formula (VIII) wherein Z is hydroxy, is preferably carried out in an organic solvent, e.g. dimethylsulfoxide, dimethylformamide, ethanol, benzene or pyridine, in the presence of an organic or inorganic base, e.g. triethylamine, diisopropylethylamine, sodium or potassium carbonate or bicarbonate, and in the presence of a condensing agent, e.g. N-ethyl-N'-dicyclohexylcarbodiimide and/or hydroxybenzotriazole hydrate.

The reaction temperature may vary from about −10° C. to about

Analogous operative conditions apply when using the compounds of formula (VIII) wherein Z is a halogen atom, preferably bromine or chlorine.

The reaction, in particular, is carried out in an organic solvent such as dimethylformamide, dioxane, pyridine, benzene, tetrahydrofuran, or aqueous admixtures thereof, optionally in the presence of a base.

The reaction is carried out at temperatures varying from about 0° C. to about 100° C. and for a time varying from about 2 hours to about 48 hours.

The optional conversion of a compound of formula (VII) into a pharmaceutically acceptable salt thereof may be carried out by conventional methods.

The intermediate compounds of formula (VIII) are known or easily prepared according to known methods, for (I)

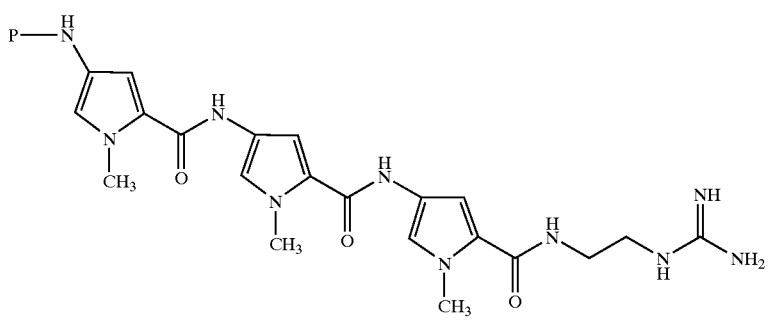

wherein P is hydrogen;

instance as reported in the aforementioned patent applications.

According to this latter aspect of the invention, preferred distamycin-guanidines thus obtainable are those wherein the R group comprises an α-bromo- or α-chloro-acryloyl moiety. Particularly preferred is the aforementioned α-bromo-acryloyl-distamycin derivative PNU 166196.

According to a preferred embodiment of the invention for preparing PNU 166196, a proper amount of distamycin A is hydrolysed under basic conditions so as to obtain the corresponding amino derivative which is then conventionally protected, for instance as tert-butoxycarbonylamino derivative (II). This latter is then reacted with a proper amount, for instance a slight excess, of (DPPA) to obtain the novel derivative of formula (III). The compound of formula (III) is then hydrolysed under basic conditions to the compounds of formula (IV) which, properly deprotected according to conventional methods, are then reacted with a suitable amount, for instance in a molar ratio (I):(VII) comprised from 1:1 to 1:2, of 1-methyl-4-(α-bromoacryloylamido) pyrrole-2-carbonyl chloride of formula (VII), so as to obtain the desired compound.

With the aim of better illustrating the present invention without posing any limitation to it, herewith provided are the following examples.

EXAMPLE 1

Preparation of N-[(4-{[(4-{[(4-amino-1-methyl-1H-pyrrol-2-yl)carbonyl]amino}-1-methyl-1H-pyrrol-2-yl)carbonyl]amino}-1-methyl-1H-pyrrol-2-yl)carbonyl]-beta-alanine hydrochloride To a solution of distamycin A (10 g) in methanol (400 ml), 20% NaOH (40 ml) was added. The reaction was refluxed for 24 hours and then acidified with 37% HCl. The organic solvent was allowed under vacuum yielding a hazel precipitate that was washed with cold water (100 ml). The solid was dried under vacuum yielding the title compound (9 g; y=95%) as a brown powder.

FAB-MS: m/z 456 (100, [M+H]$^+$)

PMR (DMSO-d$_6$) δ: 10.10 (s, 1H), 9.94 (bs, 4H), 8.05 (bt, J=5.1 Hz, 1H), 7.26 (d, J=1.8 Hz, 1H), 7.19 (d, J=1.8 Hz, 1H), 7.12 (d, J=1.8 Hz, 1H) 7.05 (d, J=1.8 Hz, 1H), 7.00 (d, J=1.8 Hz, 1H), 6.86 (d, J=1.8 Hz, 1H), 3.90 (s, 3H), 3.85 (S, 3H), 3.80 (s, 3H), 3.40-3.20 (m, 2H), 2.48-2.41 (m, 2H).

EXAMPLE 2

Preparation of N-{[4-({[4-({[4-(formylamino)-1-methyl-1H-pyrrol-2-yl]carbonyl}amino)-1-methyl-1H-pyrrol-2-yl]carbonyl}amino)-1-methyl-1H-pyrrol-2-yl]carbonyl}-beta-alanine A solution of the compound obtained in example 1 (4 g), formamide (12 ml) and ethyl formate (12 ml) was stirred at 90° C. for 5 hours. The organic solvent was allowed under vacuum, the brown residue treated with water (100 ml) and the suspension stirred for one hour. The suspension was filtered and the solid washed with cold water (20 ml) yielding, after desiccation under vacuum at 40° C., the title compound (6.8 g; y=90%) as a brown powder.

FAB-MS: m/z 482 (100, [M+H]$^+$); 359 (15, [M+H—NH$_2$(CH$_2$)$_2$COOH]$^+$) PMR (DMSO-d$_6$): 10.10 (s, 1H), 9.95 (s, 1H), 9.92 (s, 1H), 8.13 (s, 1H), 8.05 (bt, J=5.1 Hz, 1H), 7.24 (d, J=1.8 Hz, 1H), 7.21 (d, J=1.8 Hz, 1H), 7.19 (d, J=1.8 Hz, 1H) 7.04 (d, J=1.8 Hz, 1H), 6.92 (d, J=1.8 Hz, 1H), 6.86 (d, J=1.8 Hz, 1H), 3.84 (s, 3H), 3.82 (s, 3H), 3.80 (s, 3H), 3.40-3.20 (m, 2H), 2.46-2.42 (m, 2H).

EXAMPLE 3

Preparation of N-({4-[({4-[({4-[(tert-butoxycarbonyl)amino]-1-methyl-1H-pyrrol-2-yl}carbonyl)amino]-1-methyl-1H-pyrrol-2-yl}carbonyl)amino]-1-methyl-1H-pyrrol-2-yl}carbonyl)-beta-alanine To a solution of the compound of example 1 (7 g) in dry DMF (150 ml), TEA (4 ml) and di-tert-butyldicarbonate (6.2 g) were added. After 3 hours, water (100 ml) was added and the solution stirred for further 30 minutes. The DMF was allowed under vacuum, the aqueous phase was acidified to pH=4 with 1% CH$_3$COOH and the suspension was stirred for about 1 hour. The suspension was filtered and the solid washed with water (100 ml) yielding, after desiccation under vacuum at 40° C., the title compound (6.8 g; y=90%) as a brown powder.

FAB-MS: m/z 556 (100, [M+H]$^+$); 500 (15, [M+H—(CH$_3$)$_2$—CH—CH$_2$]$^+$); 456 (35, [M+H—(CH$_3$)$_2$—CH—CH$_2$—CO$_2$]$^+$)

PMR (DMSO-d$_6$) δ: 9.84 (s, 1H), 9.82 (s, 1H), 9.05 (s, 1H), 7.98 (t, J=5.8 Hz, 1H), 7.19 (d, J=1.7 Hz, 1H), 7.16 (d, J=1.7 Hz, 1H), 7.01 (d, J=1.7 Hz, 1H) 6.87 (bs, 1H), 6.83 (d, J=1.7 Hz, 1H), 6.82 (bs, 1H), 3.82 (s, 3H), 3.79 (s, 3H), 3.78 (s, 3H), 3.39-3.32 (m, 2H), 2.43–2.48 (m, 2H), 1.44 (s, 9H).

EXAMPLE 4

Preparation of tert-butyl 1-methyl-5-[({1-methyl-5-[({1-methyl-5-[(2-oxo-1-imidazolidinyl)carbonyl]-1H-pyrrol-3-yl}amino)carbonyl]-1H-pyrrol-3-yl}amino)carbonyl]-1H-pyrrol-3-ylcarbamate To a solution of the compound of example 3 (6.5 g), in dry DMF (100 ml) warmed to 80° C., TEA (1.8 ml) and DPPA (2.77 ml) were added dropwise. The solution was stirred at 80° C. for five hours. The solution was concentrated under vacuum and 2% CH$_3$COOH solution (200 ml) was added. The suspension was stirred for one hour, the aqueous phase removed by filtration and the precipitate washed with water (100 ml). Desiccation under vacuum at 50° C. yielded the title compound (4.2 g; y=65%) as a hazel powder.

FAB-MS: m/z 553 (60, [M+H]$^+$)

PMR (DMSO-d$_6$) δ: 9.87 (s, 1H), 9.83 (s, 1H), 9.05 (s, 1H), 7.50 (bs, 1H), 7.35 (d, J=1.7 Hz, 1H), 7.19 (d, J=1.7 Hz, 1H), 7.03 (d, J=1.7 Hz, 1H), 6.87 (bs, 1H), 6.81 (bs, 1H), 6.72 (d, J=1.7 Hz, 1H), 3.85-3.80 (m, 2H), 3.82 (s, 3H), 3.79 (s, 3H), 3.70 (s, 3H), 3.32–3.37 (m, 2H), 1.44 (s, 9H). By an analogous procedure and by using the opportune starting materials the following compound was obtained: 1-methyl-N-{1-methyl-5-[({1-methyl-5-[(2-oxo-1-imidazolidinyl)carbonyl]-1H-pyrrol-3-yl}amino)carbonyl]-1H-pyrrol-3-yl}-4-(2-oxoethyl)-1H-pyrrole-2-carboxamide FAB-MS: m/z 481 (100, [M+H]$^+$)

PMR (DMSO-d$_6$) δ: 10.05 (s, 1H), 9.93 (s, 1H), 9.92 (s, 1H), 8.14 (m, 1H), 7.55 (bs, 1H), 7.39 (d, J=1.7 Hz, 1H), 7.24 d, J=1.7 Hz, 1H), 7.21 (d, J=1.7 Hz, 1H), 7.08 (d, J=1.7 Hz, 1H), 6.92 (d, J=1.7 Hz, 1H), 6.78 (d, J=1.7 Hz, 1H), 3.88-3.82 (m, 2H), 3.86 (s, 3H), 3.85 (s, 3H), 3.74 (s, 3H), 3.38–3.42 (m, 2H).

EXAMPLE 5

Preparation of tert-butyl 5-{[(5-{[(5-{[(2-aminoethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-ylcarbamate trifluoroacetate To a solution of compound of example 4 (3 g), in dry DMF (50 ml), 1N NaOH (7.5 ml) and water (3 ml) were added and the solution was stirred at room temperature for 2 hours. The organic solvent was removed under vacuum and water (60 ml) was added. The mixture was then extracted with ethyl acetate (3×150 ml), the combined organic phases were dried ($Na_2SO_4$), acidified with trifluoroacetic acid and concentrated in vacuum yielding the title compound (1.7 g, y=54%) as a yellow powder.

FAB-MS: m/z 527 (100, [M+H]$^+$), 471 (35), 427 (55)

PMR (DMSO-d$_6$) δ: 9.85 (s, 1H), 9.82 (s, 1H), 9.05 (s, 1H), 8.01 (t, J=5.6 Hz, 1H), 7.19 (d, J=1.7 Hz, 1H), 7.16 (d, J=1.7 Hz, 1H), 7.02 (d, J=1.7 Hz, 1H), 6.89 (d, J=1.7 Hz, 1H), 6.87 (bs, 1H), 6.82 (bs, 1H), 3.82 (s, 3H), 3.79 (s, 3H), 3.78 (s, 3H), 3.26-3.20 (m, 2H), 2.74 (t, J=5.6 Hz, 1H).

By an analogous procedure and by using the opportune starting materials the following compounds was obtained:
N-(5-{[(5-{[(2-aminoethyl)amino]carbonyl}-1-methyl-1H-pyrrol-3-yl)amino]carbonyl}-1-methyl-1H-pyrrol-3-yl)-4-(formylamino)-1-methyl-1H-pyrrole-2-carboxamide trifluoroacetate

EXAMPLE 6

Preparation of tert-butyl 5-{[(5-{[(5-{[(2-{[t-butoxycarbonylamino(t-butoxycarbonylimino)methyl] amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-ylcarbamate To a solution of the compound of example 6 (2 g), TEA (860 µl) in EtOH (30 ml), N,N'-di-tert-butoxycarbonyl-N"triflylguanidine (1 g), prepared as reported in *J. Org. Chem.* 1998, 63, 3804–3805, was added. The mixture was stirred at 40° C. for 3 hours, the solvent evaporated under vacuum and the residue purified by flash chromatography (DCM-methanol 9:1) yielding the title compound (1.6 g, y=90%) as a ivory powder.

FAB-MS: m/z 769 (40, [M+H]$^+$), 669 (20)

PMR (DMSO-d$_6$) δ: 11.47 (s, 1H), 9.84 (s, 1H), 9.82 (s, 1H), 9.05 (bs, 1H), 8.39 (t, J=5.4 Hz, 1H), 8.08 (t, J=5.4 Hz, 1H), 7.19 (d, J=1.7 Hz, 1H), 7.15 (d, J=1.7 Hz, 1H), 7.01 (d, J=1.7 Hz, 1H), 6.86 (m, 2H), 6.82 (bs, 1H), 3.82 (s, 3H), 3.79 (s, 3H), 3.78 (s, 3H), 3.48-3.40 (m, 2H), 3.33 (t, J=5.4 Hz, 2H), 1.45 (s, 9H), 1.44 (s, 9H), 1.38 (s, 9H).

By an analogous procedure and by using the opportune starting materials the following compounds was obtained:
N-(5-{[(5-{[(2-{[t-butoxycarbonylamino(t-butoxycarbonyl imino)methyl]amino}ethyl)amino]carbonyl}-1-methyl-1H-pyrrol-3-yl)amino]carbonyl}-1-methyl-1H-pyrrol-3-yl)-4-(formyl amino)-1-methyl-1H-pyrrole-2-carboxamide

EXAMPLE 7

Preparation of 4-amino-N-(5-{[(5-{[(2-{[amino (imino) methyl]amino}ethyl)amino]carbonyl}-1-methyl-1H-pyrrol-3-yl) amino]carbonyl}-1-methyl-1H-pyrrol-3-yl)-1-methyl-1H-pyrrole-2-carboxamide dihydrochloride The compound of example 6 (1.5 g) was dissolved in HCl/EtOH solution (20 ml), and stirred at room temperature for 12 hours. The solvent was evaporated under vacuum yielding the title compound (950 mg, y=90%) as a brown powder.

FAB-MS: m/z 469, (15, [M+H]$^+$)

PMR (DMSO-d$_6$) δ: 10.38-10.11 (b.s., 4H), 9.98 (s, 1H), 8.28 (b.s., 1H), 8.19 (d, J=1.7 Hz, 1H), 7.73, (b.s., 1H), 7.63 (d, J=1.7 Hz, 1H), 7.60-7.00 (b.s., 4H), 7.28 (d, J=1.7 Hz, 1H), 7.20 (d, J=1.7 Hz, 1H), 7.1 (d, J=1.7 Hz, 1H), 6.92 (d, J=1.7 Hz, 1H), 3.93 (s, 3H), 3.90 (s, 3H), 3.82 (s, 3H), 3.28 (m, 4H).

EXAMPLE 8

N-(5-{[(5-{[(5-{[(2-{[amino(imino)methyl] amino}ethyl) amino]carbonyl}-1-methyl-1H-pyrrol-3-yl)amino]carbonyl}-1-methyl-1H-pyrrol-3-yl) amino]carbonyl}-1-methyl-1H-pyrrol-3-yl)-4-[(2-bromoacryloyl)amino]-1-methyl-1H-pyrrole-2-carboxamide (internal code PNU 166196)

A solution of 500 mg of 1-methyl-4-(α-bromoacrylamido)pyrrole-2-carboxyl chloride, prepared as reported in WO 98/04524, in 15 ml of benzene, was added to a solution of the compound of example 6 (500 mg) and 164 mg of $NaHCO_3$ in 5 ml of $H_2O$. The solution was vigorously stirred for 8 hours at room temperature, then evaporated under vacuum and the crude residue was purified by flash chromatography (methylene chloride/methanol: 8/2) to yield 440 mg of the title compound as a yellow solid.

FAB-MS: m/z 723, (32, [M+H]$^+$)

PMR (DMSO-d$_6$) δ: 10.30 (s, 1H), 9.95 (s, 1H), 9.92 (s, 1H), 9.90 (s, 1H), 8.10 (t, J=5.9 Hz, 1H), 7.56 (t, J=5.9, 1H), 7.2 (b.s., 4H), 6.9–7.3 (m, 8H), 6.68 (d, J=2.9 Hz, 1H), 6.21 (d, J=2.9 Hz, 1H), 3.85 (s, 3H), 3.84 (s, 3H), 3.83 (s, 3H), 3.80 (s, 3H), 3.30 (b.s., 4H).

What is claimed is:

1. A process for preparing a poly-pyrroleamido derivative of formula

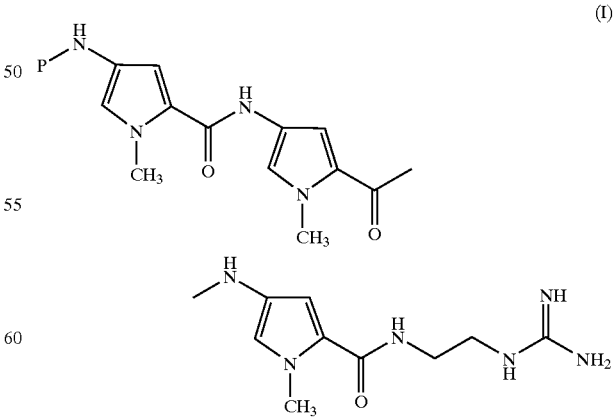

(I)

wherein P is a hydrogen atom or a suitable amino protecting group, which process comprises:

a) hydrolysing distamycin A under basic conditions and properly protecting the resulting amino group so as to obtain a compound of formula

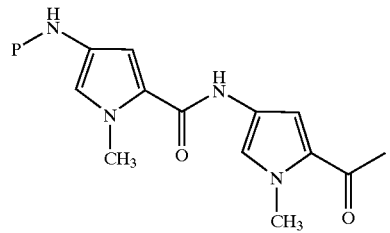

(II)

wherein P is a suitable amino protecting group;

b) reacting the compound of formula (II) with diphenylphosphorylazide (DPPA), so as to obtain a compound of formula

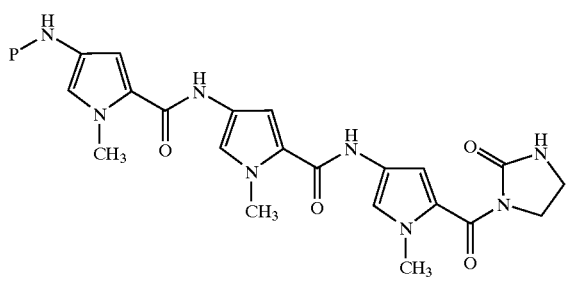

(III)

c) hydrolysing under basic conditions the compound of formula (III) so as to obtain the derivative of formula

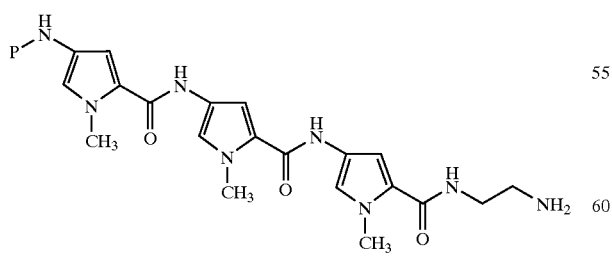

(IV)

d) reacting the compound of formula (IV) with a suitable guanylating agent so as to obtain the derivative of formula

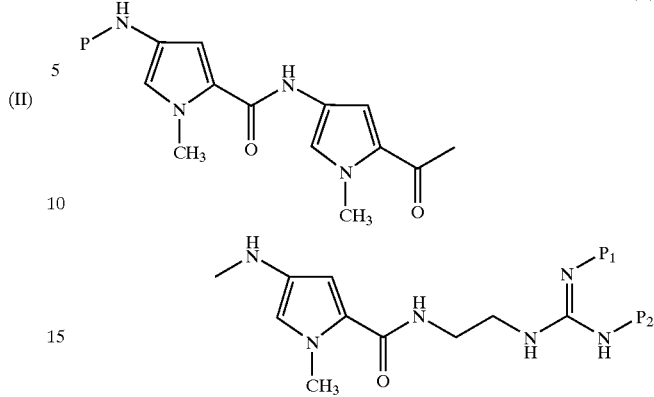

(V)

wherein $P_1$ and $P_2$, the same, are hydrogen atoms or amino protecting groups equal or different to P; and when $P_1$ and $P_2$ are other than hydrogen atoms, e) deprotecting the guanidino and the amino group so as to obtain the derivative of formula (I).

2. A process according to claim 1 wherein the amino protecting groups P, $P_1$ and $P_2$ are selected from formyl, benzyl and tert-butoxycarbonyl.

3. A process according to claim 2 wherein the amino protecting group is tert-butoxycarbonyl.

4. A process according to claim 1 wherein, in step (d), suitable guanylating agents are selected from the group consisting of S-methylisothiourea, O-methylisourea, 3,5-dimethylpyrazole-1-carboxamidine or N-N'-di-tert-butoxycarbonyl-N"triflylguanidine of formula

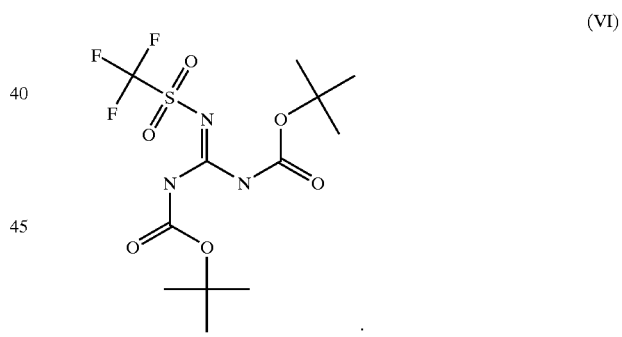

(VI)

5. A compound of formula

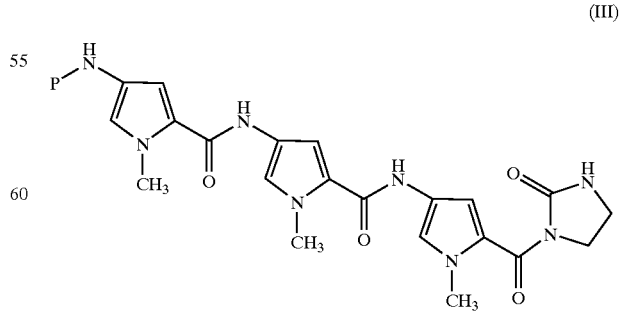

(III)

wherein P is hydrogen or a suitable amino protecting group.

6. A compound of claim 5 wherein P is formyl, benzyl or tert-butoxycarbonyl.

7. A compound of claim 6 wherein P is tert-butoxycarbonyl.

8. A process for preparing distamycin-guanidines of formula

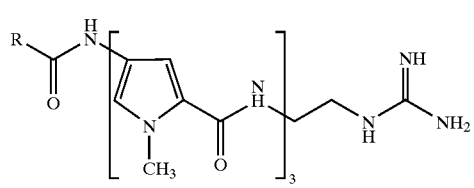

(VII)

wherein
R is selected from the group consisting of:

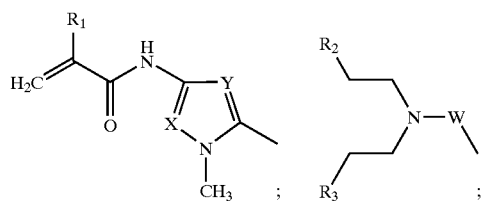

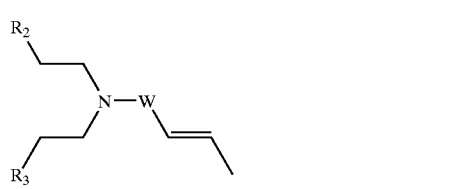

wherein
$R_1$ and $R_2$ are chlorine or bromine atoms;
$R_3$ is hydrogen, chlorine or bromine;
X and Y, the same or different, are selected from nitrogen or CH groups;
W is phenylene or a benzocondensed 5 or 6 membered heterocycle with 1 or 2 heteroatoms selected among N, O or S, both of which being optionally further substituted by lower alkyl groups; or pharmaceutically acceptable salts thereof; which process comprises:
a) hydrolysing distamycin A under basic conditions and properly protecting the resulting amino group so as to obtain a compound of formula

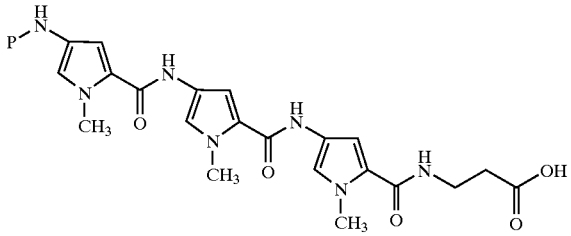

(II)

wherein P is a suitable amino protecting group;
b) reacting the compound of formula (II) with diphenylphosphorylazide (DPPA), so as to obtain a compound of formula

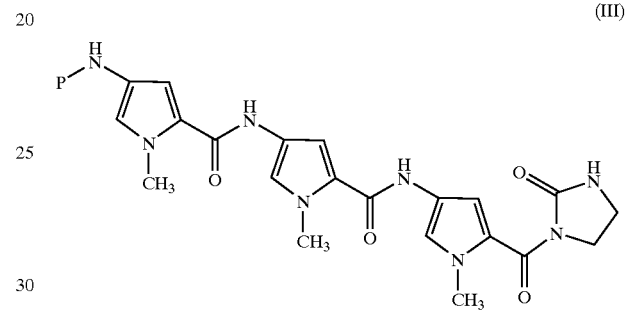

(III)

c) hydrolysing under basic conditions the compound of formula (III) so as to obtain the derivative of formula

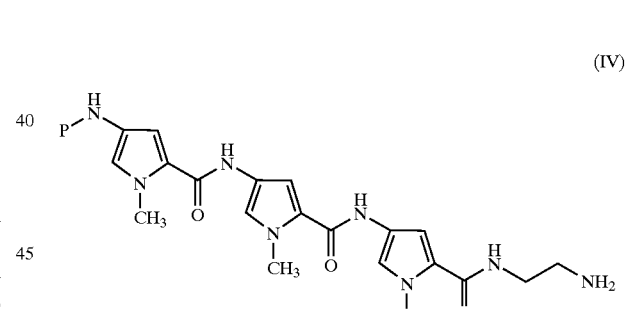

(IV)

d) reacting the compound of formula (IV) with a suitable guanylating agent so as to obtain the derivative of formula

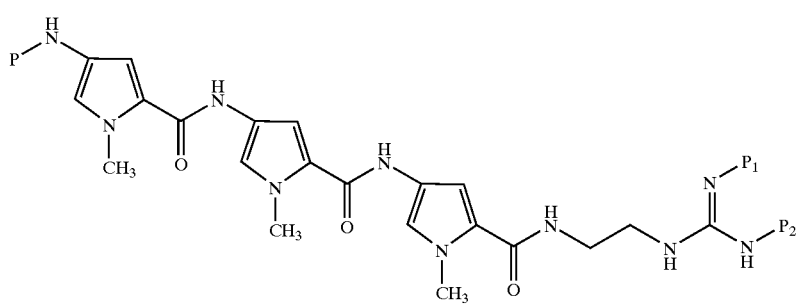

(V)

wherein $P_1$ and $P_2$ are the same, are hydrogen atoms or amino protecting groups equal or different to P; and when $P_1$ and $P_2$ are other than hydrogen atoms, e) deprotecting the guanidino and the amino group so as to obtain the derivative of formula

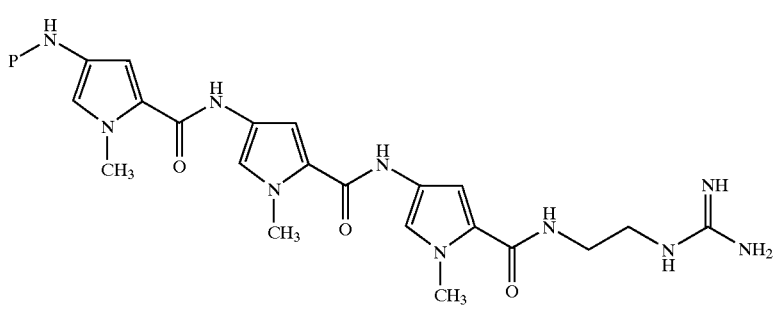

wherein P is hydrogen;

f) acylating the compound of formula (I) with a carboxylic derivative of formula

R-COZ  (VIII)

wherein R has the above reported meanings and Z is hydroxy or a suitable leaving group, so as to obtain the compounds of formula (VII) and, whenever desired, converting them into pharmaceutically acceptable salts.

9. A process according to claim 8 wherein Z, within the compound of formula (VIII), is selected from hydroxy, bromine or chlorine.

10. A process according to claim 8 for preparing a compound of formula

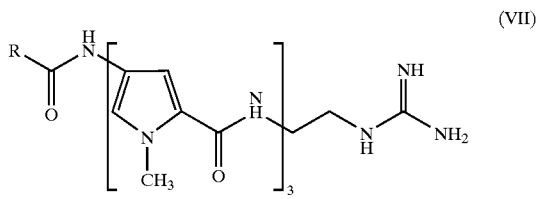

wherein

R is a group of formula:

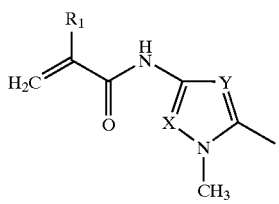

wherein $R_1$ is a chlorine or bromine atoms;

X and Y, the same or different, are selected from nitrogen or CH groups; or pharmaceutically acceptable salts thereof.

11. A process according to claim 8 for preparing a compound, optionally in the form of a pharmaceutically acceptable salts selected from the group consisting of:

N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-chloroacryloyl)amino]-1-methyl-1H-pyrrole-2-carboxamide; (internal code PNU 166196);

N-(5-{[(5-{[(5-{[(2-{[amino(imino)methyl[amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-chloroacryloyl)amino]-1-methyl-1H-pyrrole-2-carboxamide;

N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide;

N-(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl -1H-pyrrol-3-yl)-3-[(2-bromoacryloy)amino]-1-methyl-1H-pyrorrol-5-carboxamide;

N-(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)-4-({[4-({4-[bis(2-chloroethyl)amino]benzoyl}amino)-1-methyl-1H-pyrrol-2-yl]carbonyl}amino)-1-methyl-1H-pyrrole-2-carboxamide;

N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-({4-[bis(2-chloroethyl)amino]benzoyl}amino)-1-methyl-1H-pyrazole-5-carboxamide; and N-(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)-4-[({4-[(-3-{4-[bis(2-chloroethyl)amino]phenyl}-2-propenoyl)amino]-1-methyl-1H-pyrrol-2-yl}carbonyl)amino]-1-methyl-1H-pyrrole-2-carboxamide.

* * * * *